US012778679B2

(12) United States Patent
Barthel et al.

(10) Patent No.: US 12,778,679 B2
(45) Date of Patent: Nov. 3, 2026

(54) SYSTEM TO DISPLAY CLIP POSITIONS BASED ON TRACING VESSELS

(71) Applicant: Verb Surgical Inc., Santa Clara, CA (US)

(72) Inventors: Alexander Barthel, Munich (DE); Ashwath Narayan Murali, Santa Clara, CA (US); Bernhard A. Fuerst, Munich (DE); Risto Kojcev, Santa Clara, CA (US); Kristina Yevseyeva, Santa Clara, CA (US)

(73) Assignee: Auris Health, Inc., Santa Clara, CA (US)

(*) Notice: Subject to any disclaimer, the term of this patent is extended or adjusted under 35 U.S.C. 154(b) by 125 days.

(21) Appl. No.: 18/310,714

(22) Filed: May 2, 2023

(65) Prior Publication Data

US 2024/0366305 A1 Nov. 7, 2024

(51) Int. Cl.

| | |
|---|---|
| ***A61B 34/10*** | (2016.01) |
| ***G06T 17/00*** | (2006.01) |
| ***G06T 19/00*** | (2011.01) |
| *A61B 90/00* | (2016.01) |

(52) U.S. Cl.

CPC .............. *A61B 34/10* (2016.02); *G06T 17/00* (2013.01); *G06T 19/00* (2013.01); *A61B 2034/104* (2016.02); *A61B 2034/105* (2016.02); *A61B 2034/107* (2016.02); *A61B 2090/371* (2016.02); *A61B 2090/372* (2016.02); *G06T 2200/24* (2013.01); *G06T 2210/41* (2013.01); *G06T 2219/004* (2013.01)

(58) Field of Classification Search

CPC .............. A61B 34/10; A61B 2034/104; A61B 2034/105; A61B 2034/107; A61B 2090/371; A61B 2090/372; A61B 17/122; G06T 17/00; G06T 19/00; G06T 2200/24; G06T 2210/41; G06T 2219/004

See application file for complete search history.

(56) References Cited

U.S. PATENT DOCUMENTS

2010/0312072 A1* 12/2010 Breskin .................. A61B 6/485 600/300

2011/0060446 A1 3/2011 Ono (Continued)

OTHER PUBLICATIONS

Extended European Search Report received for EP Patent Application No. 24173632.1, mailed on Aug. 22, 2024, 8 pages.

(Continued)

*Primary Examiner* — Kent W Chang

*Assistant Examiner* — Karl Dug Truong

(74) *Attorney, Agent, or Firm* — Aikin & Gallant, LLP

(57) ABSTRACT

A system includes a display, and a processor. The processor may be configured to obtain a three-dimensional model of a patient including one or more blood vessels and a mass that is marked for removal, determine a position of each of one or more surgical clips within the three-dimensional model, where blood flow is restricted from a region of the three-dimensional model based on the one or more blood vessels of the three-dimensional model and the position of each of the one or more surgical clips, and present, to the display, the three-dimensional model of the patient including a visual indication of the region and the mass.

20 Claims, 6 Drawing Sheets

(56) References Cited

U.S. PATENT DOCUMENTS

| | | | | |
|---|---|---|---|---|
| 2013/0116748 | A1* | 5/2013 | Bokil | A61N 1/36182<br>607/59 |
| 2014/0333617 | A1* | 11/2014 | Miyamoto | A61B 34/10<br>345/420 |
| 2015/0127316 | A1 | 5/2015 | Avisar | |
| 2015/0324114 | A1* | 11/2015 | Hurley | G16Z 99/00<br>715/850 |
| 2016/0171157 | A1* | 6/2016 | Mielekamp | A61B 6/463<br>345/589 |
| 2016/0242855 | A1* | 8/2016 | Fichtinger | A61B 17/320016 |
| 2017/0035517 | A1* | 2/2017 | Geri | A61B 90/37 |
| 2019/0279416 | A1* | 9/2019 | Lee | G06T 19/20 |
| 2021/0236213 | A1* | 8/2021 | Sorger | A61B 34/10 |
| 2021/0236233 | A1* | 8/2021 | Fuerst | A61B 34/37 |
| 2022/0370138 | A1* | 11/2022 | Shelton, IV | A61B 34/25 |
| 2024/0024029 | A1* | 1/2024 | Kopel | A61B 34/10 |
| 2024/0050160 | A1* | 2/2024 | Adebar | A61B 90/361 |
| 2024/0298967 | A1* | 9/2024 | Bueno | A61B 5/1076 |

OTHER PUBLICATIONS

Sook Kien Ng et al., "Automation of clip localization in Digital Tomosynthesis for setup of Breast Cancer Patients", dated Jun. 15, 2011, 8 pages.

* cited by examiner

CLIP SELECTION PROCESS 502

```
FOR each clip in clip list
    calculate Mass Volume (MV) and Healthy Volume (HV)
END FOR
SORT clip list in decreasing order of MV/HV
SET MV_Threshold to 1.0
SET HV_Threshold to 0.1
SET ACCUMULATED_HV to 0.0
SET ACCUMULATED_MV to 0.0
SET SELECTED_CLIPS to empty
WHILE (ACCUMULATED_HV < HV_Threshold) and (ACCUMULATED_MV < MV_Threshold)
    select clip with highest MV/HV ratio
    update ACCUMULATED_HV and ACCUMULATED_MV
    add clip to SELECTED_CLIPS
    IF (ACCUMULATED_HV < HV_Threshold) and (ACCUMULATED_MV >= MV_Threshold)
        BREAK
    ENDIF
END WHILE
RETURN SELECTED_CLIPS
```

FIG. 5

SYSTEM TO DISPLAY CLIP POSITIONS BASED ON TRACING VESSELS

TECHNICAL FIELD

This disclosure relates to the field of surgical robotics and, more particularly, to displaying and interacting with three-dimensional imagery of a patient in relation to a surgical clip.

BACKGROUND

Minimally invasive surgery (MIS), such as laparoscopic surgery, involves techniques intended to reduce tissue damage during a surgical procedure. For example, laparoscopic procedures typically involve creating several small incisions in the patient (e.g., in the abdomen), and introducing one or more tools and at least one endoscopic camera through the incisions into the patient. The surgical procedures are then performed by using the introduced tools, with the visualization aid provided by the camera.

MIS provides multiple benefits, such as reduced patient scarring, less patient pain, shorter patient recovery periods, and lower medical treatment costs associated with patient recovery. In some embodiments, MIS may be performed with surgical robotic systems that include one or more robotic arms for manipulating surgical instruments based on commands from an operator. For example, an operator may provide commands for manipulating surgical instruments, while viewing an image that is provided by a camera and displayed on a display to the user.

Under surgical operations (e.g., MIS operations), one or more clips may be applied to targeted locations on a patient to help perform a surgical operation. A clip may be referred to as a surgical clip or a ligation clip. A clip may be applied during surgery to a blood vessel to reduce or stop blood flow to a region of the patient, or to hold patient tissue to improve access to tissue or mass, or both.

SUMMARY

Systems and methods described in the present disclosure may determine and provide optimal surgical clip placement to help reduce the amount of healthy tissue that is removed. It may also reduce the chance of human error, by determining potential clip candidates that may otherwise be missed through manual inspection.

In one aspect, a method includes obtaining or constructing a three-dimensional model of a patient including one or more blood vessels and a mass that is marked for removal, determining a position of each of one or more surgical clips within the three-dimensional model, where a region of the three-dimensional model in which blood flow is restricted based on the one or more blood vessels of the three-dimensional model and the position of each of the one or more surgical clips, and presenting, to a display, the three-dimensional model of the patient including a visual indication of the region and the mass.

In some embodiments, determining the position of each of the one or more surgical clips is determined based on user input indicating the position of each of the one or more surgical clips on a portion of the one or more blood vessels. The method may include displaying an amount of the region that is associated with the mass that is marked for removal and a second amount of the region that is associated with healthy tissue.

In some embodiments, determining the position of each of the one or more surgical clips includes automatically selecting the position of each of the one or more surgical clips among a plurality of potential positions associated with the one or more blood vessels, to increase an amount of the mass that is included in the region, and to reduce an amount of healthy tissue that is in the region. In some examples, determining the position of each of the one or more surgical clips includes selecting a first position that is associated with a highest ratio of an amount of the mass that is included in the region relative to an amount of healthy tissue that is included in the region.

Additional positions may be selected. For example, determining the position of each of the one or more surgical clips may include selecting a next position that is associated with a next highest ratio of the amount of the mass that is included in the region relative to the amount of healthy tissue that is included in the region, and repeating the selecting based on the next highest ratio, without exceeding one or more criteria. The one or more criteria may include a maximum number of allowed surgical clips. Additionally, or alternatively, the one or more criteria may include a maximum amount of healthy tissue that is allowed in the region. Determining the position of each of the one or more surgical clips may include selecting the position of each of the one or more surgical clips until a minimum portion of the mass is included in the region.

In some embodiments, determining the position of each of the one or more surgical clips includes selecting the position of each of the one or more surgical clips to not encroach on a minimum distance between the mass and the position of each of the one or more surgical clips.

In some embodiments, obtaining the three-dimensional model of the patient includes obtaining one or more computerized tomography (CT) scans of the patient, and performing segmentation on the one or more CT scans to define structures in the three-dimensional model such as, for example, the mass that is marked for removal and the one or more blood vessels of the patient.

In some embodiments, the method includes adjusting a view of the three-dimensional model to show the region in front of other structures in the three-dimensional model, based on a selection of the region. This view adjustment may be performed automatically upon user selection, without further input from the user such as dragging, pinching, or rotating of the image through a touchscreen or mouse. In some embodiments, the method includes adjusting a view of the three-dimensional model to show the region in front of other structures in the three-dimensional model, based on a tracked position of the display.

In one aspect, a system includes a display, and a processor, configured to perform the operations described above with respect to the method. Other technical features may be readily apparent to one skilled in the art from the following figures, descriptions, and claims.

BRIEF DESCRIPTION OF THE DRAWINGS

Embodiments of the invention are illustrated by way of example and not limitation in the figures of the accompanying drawings in which like references indicate similar elements.

FIG. 5 shows an example of a clip selection process, in accordance with some embodiments.

DETAILED DESCRIPTION

Figure 1:
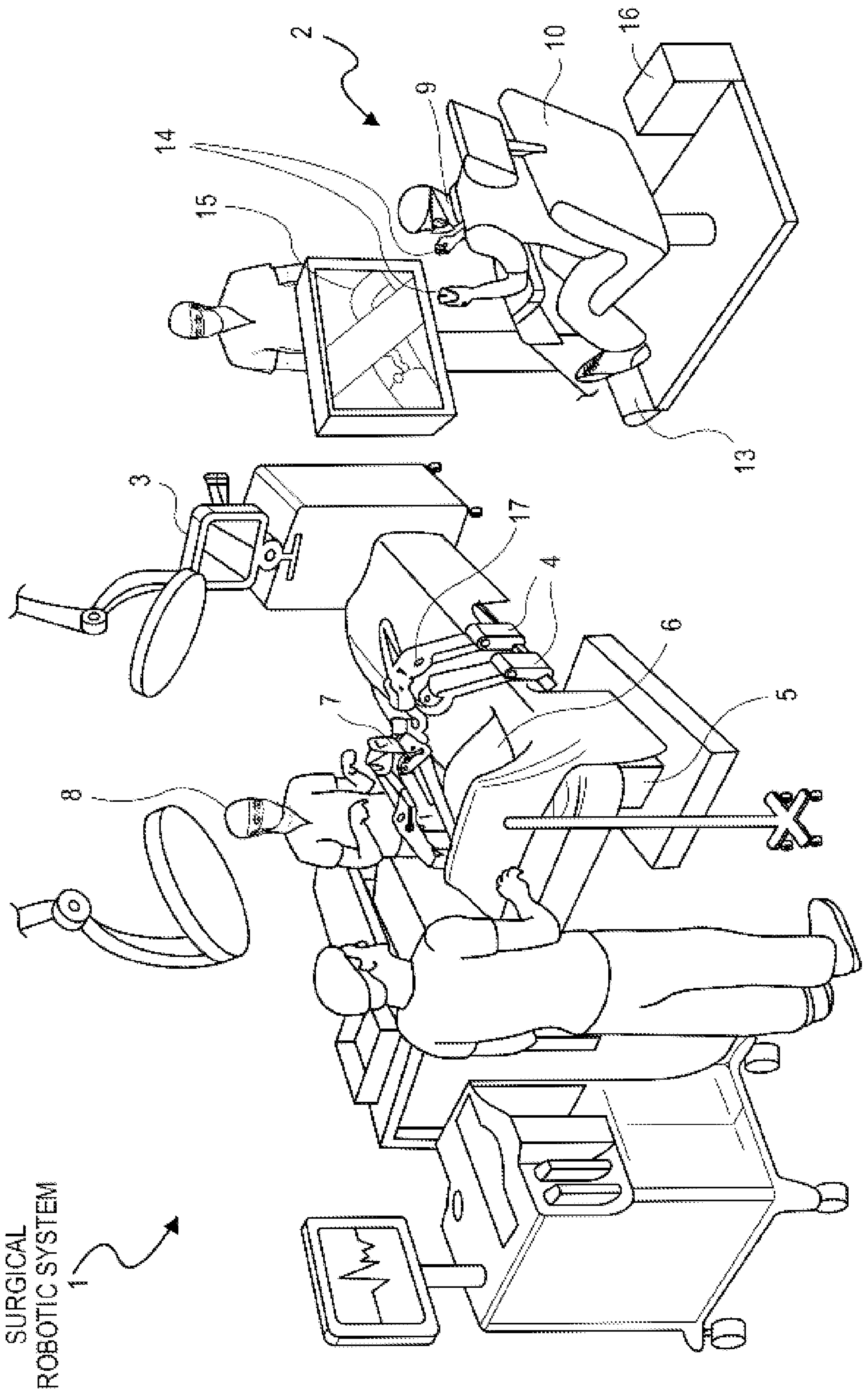
FIG. 1 is a pictorial view of an example surgical robotic system in an operating arena, according to some embodiments.

Real-time interaction with medical images may aid in performing a surgical operation. A three-dimensional reconstructed image of a patient or segmentations thereof may be displayed on a handheld tablet device or on a three-dimensional monitor (e.g., a stereoscopic display), or both. The three-dimensional patient image may be reconstructed based on one or more patient scans (e.g., with a CT).

Conventional display systems may fall short in enabling effective control of the image, or of surgical robotic systems. Furthermore, conventional display systems provide two-dimensional surgical image data to the user, and current three-dimensional displays typically require the user to wear glasses or additional, similar wearable components (e.g., with polarizing filters or dynamic shutters) for visualization of three-dimensional images. Such glasses and additional wearable components, however, may be problematic to use and manage in surgical or sterile environments. During a surgical procedure with a surgical robotic system, a surgeon may wish to view image data of the patient that can help the surgeon navigate anatomy of the patient. Thus, there is a need for improved three-dimensional display systems that enable a user to better visualize the surgical site during a surgical procedure performed with a surgical robotic system.

Existing solutions typically rely on the surgeon manually selecting the clip positions on models and picking the best clip positions for tissue removal based on the surgeon's knowledge and experience. There is room for human error, however, as suitable clip positions may be missed due to occlusion in the 3D model, or an error in judgement, or both. Additionally, some clip positions may be inadvertently ignored as they may not be near the mass, and therefore fail to provide visual cues to the user as a suitable option.

Aspects of the present disclosure automate the process of selecting clip positions in an organ or tumor. In some respects, a system or process may receive, as input, various potential clip positions and the volume of the organ they block blood flow to, and the amount of the tumor or mass that is overlapping or covered by this volume. The system or process may iterate over the potential clip positions and calculate the volume of healthy tissue in comparison to mass tissue that each clip position removes by adding the respective clip. Once this is determined, the system or process may sort the clips based on the relationship (e.g., a ratio) between the mass tissue and the healthy tissue associated with each potential clip position. The system or process may use this sorted list of clip positions to remove the maximum mass tissue and minimal healthy tissue. In some examples, finding an optimal set (e.g., one or more) of surgical clip positions may include selecting potential clip positions which are associated with a high ratio of mass tissue relative to healthy tissue. Clip positions may be selected in order of best (e.g., highest ratio of mass tissue to healthy tissue) to worst until the entire mass (or a desired amount of the mass) is covered by or occluded by the selected clip positions. The selection approach can be managed as an optimization problem where the system or process finds the minimum number of clips needed to maximize the mass tissue removed while minimizing the healthy tissue removed. This is a convex problem which may have a unique solution for a scenario based on the number of clips allowed.

Non-limiting examples of various aspects and variations of the invention are described herein and illustrated in the accompanying drawings.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure. In one aspect, the arms 4 may be mounted to a table or bed on which the patient rests as shown in the example of FIG. 1, or they may be mounted to a cart separate from the table or bed.

Each surgical tool 7 may be manipulated manually, robotically, or both, during the surgery. For example, the surgical tool 7 may be a tool used to enter, view, or manipulate an internal anatomy of the patient 6. In one embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling, or sidewall, or in another suitable structural support.

A remote operator 9, such as a surgeon or other operator, may use the user console 2 to remotely manipulate the arms 4 or the attached surgical tools 7, e.g., teleoperation. The user console 2 may be in the same operating room as the rest of the system 1, as shown in FIG. 1. In other environments, however, the user console 2 may be in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g., position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate, for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired or wireless links, using any suitable ones of a variety of data communication protocols. Any wired connections may be optionally built into the floor or walls or ceiling of the operating room. The robotic system 1 may provide video output to one or more displays, including displays within the operating room as well as remote displays that are accessible via the Internet or other networks (e.g., the robotic system 1 can include one or more endoscopic cameras that provide video output or other suitable image data to the displays). The video output or feed may also be encrypted to ensure privacy and all or portions of the video output may be saved to a server or electronic healthcare record system.

Figure 2:
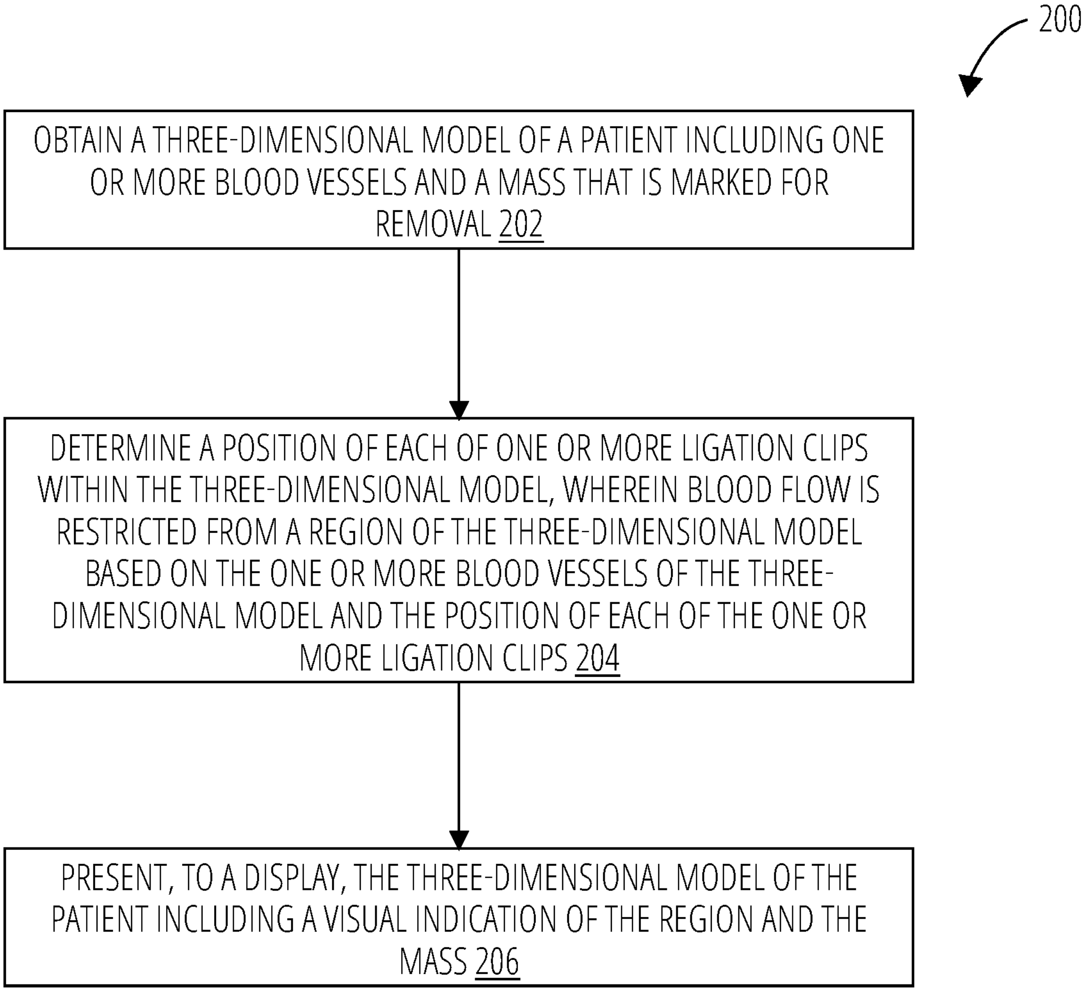
FIG. 2 shows an example method for determining a clip position, in accordance with some embodiments.

FIG. 2 shows an example method 200 for determining a clip position, in accordance with some embodiments. The method may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. Processing logic may be integral to surgical robotic system 1 such as, for example, within the user console 2, or as a separate device (e.g., a tablet computer, etc.). In some embodiments, a user such as operator 8 or operator 9 in FIG. 1 may operate such a device before or during a surgical operation.

Method 200 illustrates example functions used by various embodiments. Although specific function blocks ("blocks") are disclosed in the method, such blocks are examples. That is, embodiments are well suited to performing various other blocks or variations of the blocks recited in the method. It is appreciated that the blocks in method 200 may be performed in an order different than presented, and that not all the blocks in the method may be performed.

At block 202, method 200 obtains a three-dimensional model of a patient including one or more blood vessels and a mass that is marked for removal. The model may be determined based on CT scans. Further, the model may include segmentations that separately define the organs, the blood vessels, and the mass (e.g., a tumor) that is to be removed.

At block 204, method 200 determines a position of each of one or more surgical clips within the three-dimensional model, wherein blood flow is restricted to a region of the three-dimensional model based on the one or more blood vessels of the three-dimensional model and the position of each of the one or more surgical clips. The region may be a total region that blood flow is blocked to, because of selection of the combined positions of the one or more surgical clip.

At block 206, method 200 presents, to a display, the three-dimensional model of the patient including a visual indication of the region and the mass. The display may be integral to a mobile device, or on a stationary display. In some embodiments, the display may include a three-dimensional display (e.g., a stereoscopic display).

In some examples, at block 204, determining the position of each of the one or more surgical clips includes obtaining user input indicating the position of each of the one or more surgical clips on a portion of the one or more blood vessels. For example, the method may provide a prompt to a user to select a portion of the display corresponding to where a surgical clip is to be placed. The user may use a mouse, a touchscreen, or other user input device to select a structure to place the surgical clip on. For example, the user may select one or more portions of a blood vessel on the display to indicate a potential position that the surgical clip will be placed in. In response, the method may determine a region of the three-dimensional model that is affected by the clip. The method may trace the blood vessel to find the region that the blood vessel supplies blood to. The system may calculate a volume of that region. For example, the volume may be determined based on the size of the blood vessel or the type of blood vessel, or other factors. Thus, depending on the clip position selected by the user (e.g., on which structure of the blood vessel the clip is placed upon), the method may determine a region in the three-dimensional model (e.g., on an organ) which may be removed because of application of the clip. In some examples, the region may be contiguous. In other examples, the region may be non-contiguous (e.g., the region may include separated regions). For example, the region may be non-contiguous if various positions are selected that target different non-contiguous regions of an organ.

In some examples, the method may include displaying an amount of the region that is associated with the mass that is marked for removal, or an amount of the region that is associated with healthy tissue, or both. For example, the method may calculate a percentage or volume of the mass (e.g., y % or 'x' cubic units) that overlaps with the region that is associated with the determined clip positions, and then present this percentage or volume to the display. The percentage may be determined as the amount of mass that is in the region compared to the amount of the region that does not include the mass, or it may be determined as the amount of mass that is in the region compared to the amount of mass that is not in the region, or both.

Similarly, the method may calculate the amount of region associated with the healthy tissue as a percentage or volume of the region that overlaps with the healthy region as a percentage or volume. The percentage may be determined as the amount of healthy tissue of an organ that is in the region compared to the total amount of healthy tissue of the entire organ, or the amount of healthy tissue that is in the region compared to the amount of non-healthy tissue (e.g., mass) that is in the region.

In such a manner, the method may provide the user with how well of a job a particular clip position does at targeting removal of the mass, or of targeting mass as opposed to non-mass (e.g., healthy tissue), or both.

In some embodiments, at block 204, determining the position of each of the one or more surgical clips includes automatically selecting the position of each of the one or more surgical clips among a plurality of potential positions associated with the one or more blood vessels. The position of each of the one or more clips may be determined based on an amount of the mass that is included in the region, or the amount of healthy tissue that is in the region, or both.

For example, the position of each of the one or more surgical clips may be selected to increase an amount of the mass that is included in the region, or to reduce an amount of healthy tissue that is in the region, or both. One or more algorithms may be implemented to select an optimized or desired arrangement of one or more surgical clips, for surgery.

In some embodiments, the position of each of the one or more surgical clips may also be displayed, as well as the affected regions associated with each surgical clip, to inform the placement of the surgical clips prior to or during a surgical operation.

Figure 3:
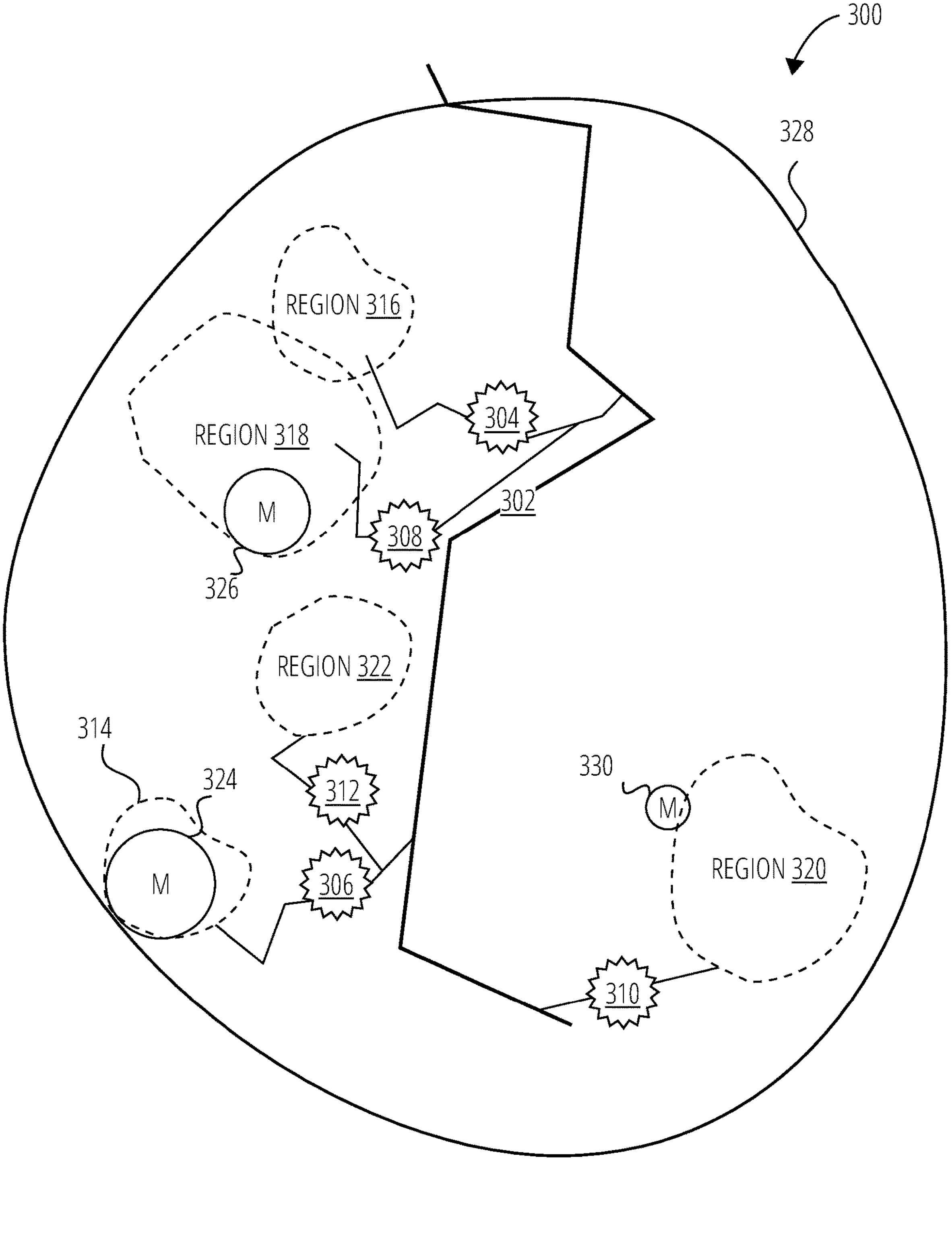
FIG. 3 shows an example of a display of a three-dimensional model of a patient, in accordance with some embodiments.

FIG. 3 shows an example of a display of a three-dimensional model 300 of a patient, in accordance with some embodiments. The display may be integral to a handheld device (e.g., a tablet computer, a laptop computer, a smartphone, etc.). Additionally, or alternatively, the display may be integral to a stationary display which may be integral to the user console of a surgical robotic system (e.g., as described with respect to FIG. 1). In some aspects, the display may include a three-dimensional display (e.g., a stereoscopic display).

The three-dimensional model 300 of the patient may be determined based on one or more computerized tomography (CT) scans of the patient. Segmentation may be performed on the one or more CT scans to define structures in the three-dimensional model such as, for example, one or more organs, one or more masses that are marked for removal, and the one or more blood vessels of the patient. Segmentation may include assigning intensities to each pixel in a 2D image, or to each voxel in a 3D image. Segmentation may include a process which may be referred to as partitioning, which is assigning a class to each pixel or voxel of those images, in structures or regions of interest. Such segmentations can be obtained through manual annotation, or automated annotation (e.g., using computer vision, a machine learning algorithm, etc.), or a combination thereof. The three-dimensional model may include one or more segmented three-dimensional images. In a three-dimensional segmentation, structure transparency, color, or brightness may be dynamically adjusted to emphasize structures of interest (less transparent, more colorful, brighter) and make others less visible (more transparent, less colorful, or less bright).

For example, in FIG. 3, a three-dimensional model may include an organ 328, blood vessel 302 which may include various branches, and a mass such as 324, 326, and 330. The mass may be identified as a suspicious mass (e.g., a growth). The mass may be contiguous or non-contiguous (as shown). Organ 328 may include a lung, a kidney, a liver, or other organ. The blood vessel or each of its branches may serve as potential positions (e.g., position 304, 306, 308, 310, or 312) that a surgical clip may be applied to.

A three-dimensional model 300 of the patient may be shown to a display. The model may include one or more blood vessels 302 and a mass (e.g., 324, 326, 330) that is marked for removal.

A position (e.g., 304, 306, 308, 310, or 312) of each of one or more surgical clips may be determined within the three-dimensional model 300. The position may be determined based on user input, or automatically (e.g., without the user selecting the clip position). For each clip position, a corresponding region (e.g., 316, 314, 318, 320, or 322) of the three-dimensional model may be determined in which blood flow is restricted due to application of the clip.

To automatically determine the clip positions, processing logic may automatically select the position of each of the one or more surgical clips among a plurality of potential positions (e.g., all potential clip branches of one or more blood vessels in a given region), based on increasing or maximizing the amount of the mass that is included in the region, or reducing or minimizing the amount of healthy tissue that is in the region, or both.

In some examples, the plurality of potential positions (e.g., 304, 306, 308, 310, or 312) may be determined based on tracing of blood vessel 302. A potential position may be generated for each branch of blood vessel 302. For example, every potential position corresponding to blood vessel 302 may be traced. From the plurality of potential positions of surgical clips, processing logic may select first position that is associated with a highest ratio of an amount of the mass that is included in the region relative to an amount of healthy tissue that is included in the region. For example, processing logic may select clip position 306 in response to region 314 having the highest ratio of mass to healthy tissue in region 314. Processing logic may select a next position (e.g., position 308) that is associated with a next highest ratio of the amount of the mass (e.g., 326) that is included in the region (e.g., region 318) relative to the amount of healthy tissue (e.g., non-mass) that is included in the region 318. Processing logic may repeat the selection process based on the next highest ratio. In some examples, this may be repeated until a minimum portion of the mass is included in the region.

For example, processing logic may select a best position/region pair based on the ratio of mass to healthy tissue, until the total mass is covered by the region. In other examples, less than the total mass may be specified. For example, a user may specify that, rather than the total mass, only 90% of the mass is to be removed. In response, processing logic may continue selecting additional best position/region pairs until 90% of the mass is covered by the respective regions.

Additionally, or alternatively, processing logic may continue selecting best position/region pairs without exceeding one or more criteria, which may be set by default or from user input, or both. In some examples, the one or more criteria may include a maximum number of allowed surgical clips. For example, a user input or setting may set the maximum number of allowed surgical clips to '2'. Processing logic may first select clip position 306 corresponding to region 314, then select clip position 308 corresponding to region 318, and stop short of selecting additional clip positions because the maximum number of allowed surgical clips may be set to '2'. Processing logic may display or emphasize the selected region (e.g., 314, 318) in the model 300.

Additionally, or alternatively, the one or more criteria may include a maximum amount of healthy tissue that is allowed in the region. For example, a user input or setting may specify that only 'x' cubic units or 'y' % of the organ is permitted to be in the total selected region. Processing logic may first select clip position/region pair 306,314 based on having the most favorable ratio. At the next pass, processing logic may determine that pair 308, 318 has the next best ratio, but selecting this pair may put the total selected region of healthy tissue beyond the maximum amount of healthy tissue allowed in the combined regions (314, 318). In response, processing logic may stop the selection process. In another embodiment, processing logic may skip this pair (308, 318) and find the next best pair (e.g., 310, 320). Processing logic may select this next pair (310, 320) so long as the maximum amount of healthy tissue that is allowed in the region is not exceeded.

In some embodiments, processing logic may select the position of each of the one or more surgical clips to not encroach on a minimum distance between the mass and the position of each of the one or more surgical clips. For example, user input or a setting may specify that the clip position is to be at least 'x' distance from the mass that is to be removed. As such, processing logic may trace positions on vessel 302 to maintain at least the minimum distance for each clip position.

In such a manner, processing logic may apply settings or user input to tailor clip selection for a given procedure or for a given patient. For example, depending on the type of procedure or the age, size, or health of the patient, it may be desirable to be more aggressive (e.g., try to remove the entire mass) or less aggressive (e.g., to not remove too much healthy tissue).

The three-dimensional model 300, which includes a visual indication of the region, and the mass may be presented to the display. The region that is visually indicated may be the region (e.g., the combined region) corresponding to the clip positions selected by user input or from the automated selection process, rather than all the regions of each potential clip position. As such, the system may provide a visual indication of the region that is to be operated.

Further, the system may display a visual indication on the three-dimensional model of each of the selected clip positions. For example, assuming that based on the selection process, only clip/region pair (306, 314) is selected. The system may display a visual indicator that indicates the boundaries of region 314, or clip position 306, or both. If multiple clips are selected, then multiple clips and their corresponding regions may each be visually indicated. The visual indication may include a boundary of the region or clip, a line, a color, an opacity, a texture difference, a brightness, or other visual indication that shows where the region starts and stops within the three-dimensional model 300. The clip position may be similarly indicated.

In such a manner, a user may be presented with surgical clip positions which may help in performing a surgical operation. The clip positions may be determined automatically in an optimized manner that may account for various settings to tailor the selection of clip positions.

Figure 4:
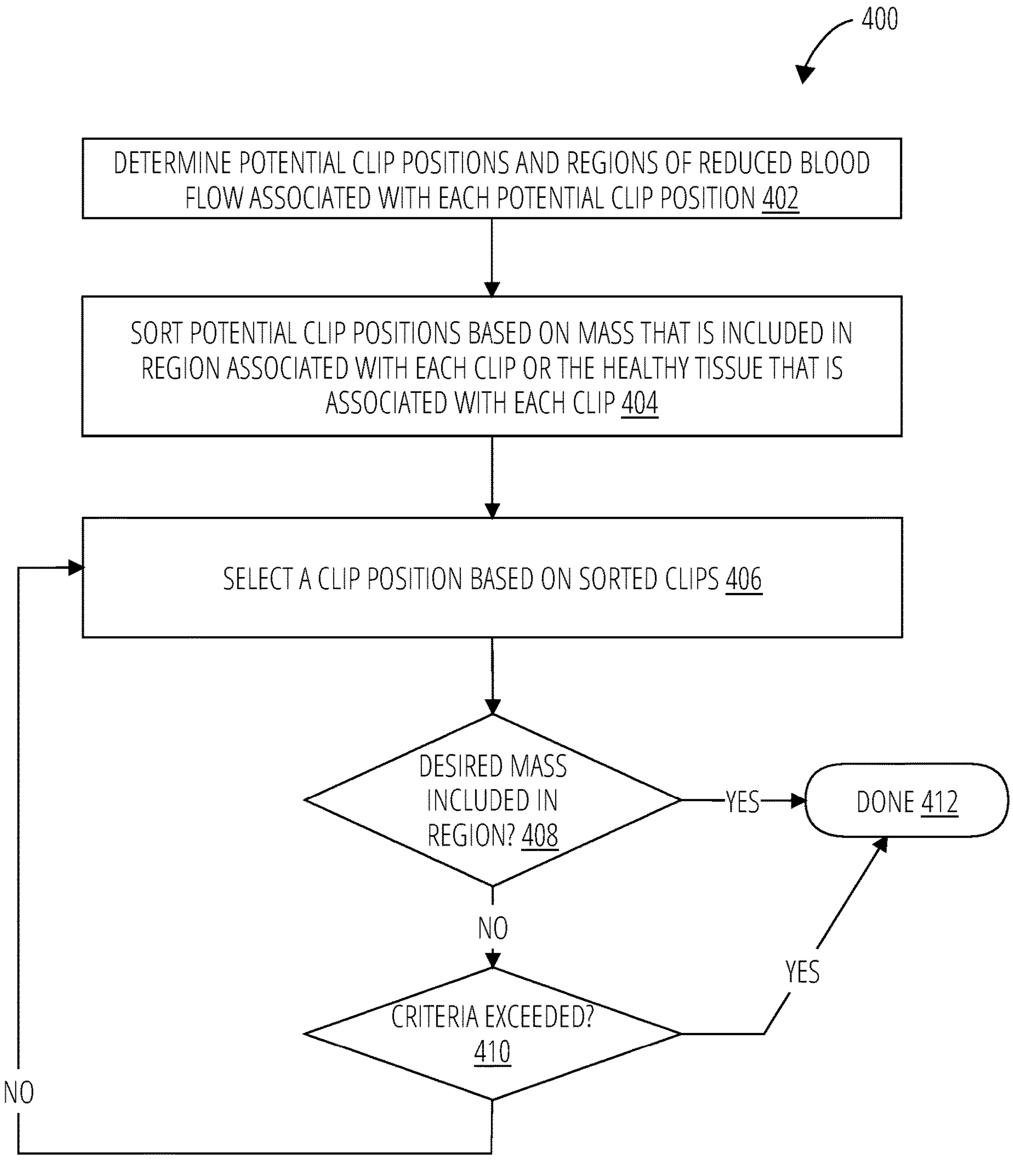
FIG. 4 shows an example flow diagram for a clip selection process, in accordance with some embodiments.

FIG. 4 shows an example flow diagram for a clip selection process 400, in accordance with some embodiments. The clip selection process 400 may be performed by processing logic, which may be integral to a computing device. The computing device may be integral to surgical robotic system 1 (e.g., user console 2), or integral to a remote device that may be used before or during an operation. The process 400 may correspond to block 204 of FIG. 2, in some embodiments.

At block 402, processing logic may determine one or more potential clip positions and regions of reduced blood flow associated with each clip position. For example, with reference to FIG. 3, processing logic may obtain the three-dimensional model and determine each clip position on one or more blood vessels (e.g., blood vessel 302). By tracing the path along each blood vessel, processing logic may determine a plurality of potential clip positions and the region associated with each clip position. In some embodiments, processing logic may determine every clip position in a region of interest (e.g., an organ). Processing logic may determine the position of each of the one or more surgical clips based on one or more settings. For example, processing logic may determine each clip position to not encroach on a minimum distance between the mass (e.g., any mass or masses) and the clip position.

At block 404, processing logic may sort each of the potential clip positions based on an amount of mass that is included in the region associated with the respective position, or the healthy tissue that is included in the region associated with the respective position, or both. For example, the potential clip positions may be sorted in order of highest (or best) having the most mass included in its affected region, or the lowest amount of healthy tissue included in its affected region, or a ratio of the two.

At block 406, processing logic may select the clip position based on the sorted clip positions determined at block 404. For example, processing logic may select the best clip position (e.g., the highest or first position in the sorted list) and then proceed to the next block 408. On subsequent iterations, the selected clip position is accumulated with previously selected clip positions. Similarly, the region associated with the selected clip may be accumulated with previously selected regions to provide a total region.

At block 408, processing logic may determine if the desired mass is included in the region (e.g., the total region). For example, settings or user input may indicate that the process is to provide clip locations that cover or occlude at least 'x' % of the total mass, or 'y' cubic units of the total mass, or all the mass. If the desired mass is included in the region, processing logic may proceed to block 412. No more clip positions will be selected. If the desired mass is not yet included in the region, processing logic may proceed to block 410.

At block 410, processing logic may determine if one or more criteria are exceeded. For example, processing logic may assess the region (e.g., the total region corresponding to all selected clips), and determine if a threshold amount of healthy tissue is included in the region. If the threshold amount of healthy tissue is included in the total region, processing logic may proceed to block 412 and be done. The amount may be a percentage (e.g., healthy tissue to overall healthy tissue of the organ) or cubic units (e.g., cubic liters, etc.), or both. Additionally, or alternatively, processing logic may determine if the maximum number of allowed clips have been selected. If so, processing logic may proceed to block 412 and be done.

At block 412, processing logic may determine whether the desired mass is included in the region. If so, processing logic may display the clip positions with the corresponding regions in the three-dimensional model. If not, processing logic may display a notification (which may be displayed) that the processed failed in finding a set of clips (e.g., one or more clip positions) that would satisfy the criteria and cover the desired mass.

If the criteria are not exceeded, and the desired mass is not included in the region, processing logic may repeat block 406 and select another clip position. Processing logic may select the next best clip position, according to the sorted clip positions from block 404. Processing logic may repeat blocks 406, 408, and 410 until the desired mass is included in the region, or until the criteria are exceeded.

FIG. 5 shows an example of a clip selection process 502, in accordance with some embodiments.

At lines L1-L3, the process 502 calculates the mass volume (MV) and healthy volume (HV) associated with each clip in the clip list. For example, referring to FIG. 3, clip position 310 may be associated with a MV that is determined as the amount of mass 330 that is included in region 320. The HV for clip position 310 may be determined as the remaining volume in region 320 which represents healthy tissue of organ 328. Some clip positions may not have mass associated with it. For example, clip position 304 may be associated with region 316. Region 316 may not contain any suspicious mass; therefore, it may have zero mass (e.g., 0% MV or 100% HV). The clip list may include an exhaustive list of potential clip positions in each region of interest.

At L4, the clip list is sorted in decreasing order, based on the ratio of mass volume (MV) to healthy volume (HV) for each clip position. For example, clip position 306 and its associated region 314 may have a MV/HV ratio of '2.1'. Clip position 308 and its associated region 318 may have a MV/HV ratio of '0.3'. Thus, clip position 306 may be listed higher (or better) than clip position 308. Clip position 304 (associated with region 316), and clip position 312 (associated with region 322) may be at the bottom of the clip list, because neither has any overlap with suspicious mass.

At L5, a threshold MV is set to a value, such as, for example, 1.0 or a different threshold. The threshold MV may control whether clips are to be selected until the total mass is included in the total region, or if just a portion of the mass is to be selected.

At L6, a threshold HV is set to a second value, such as, for example, to 0.1, or a different threshold. This may control how much healthy tissue is allowed to be removed.

At L9, a data structure that holds the selected clips is initialized to being empty.

At L10-L17, the clips are selected from the sorted clip list and placed in the data structure according to which clip has the highest ratio, while the accumulated healthy tissue volume in the total region is less than the threshold HV, and the accumulated mass volume is less than the threshold MV. If the threshold HV or threshold MV are exceeded, the process will cease selecting clips.

At L18, the data structure holding the selected clips from L10-L17 is returned. These selected clips and the accumulated region may be displayed, as described.

Figure 6:
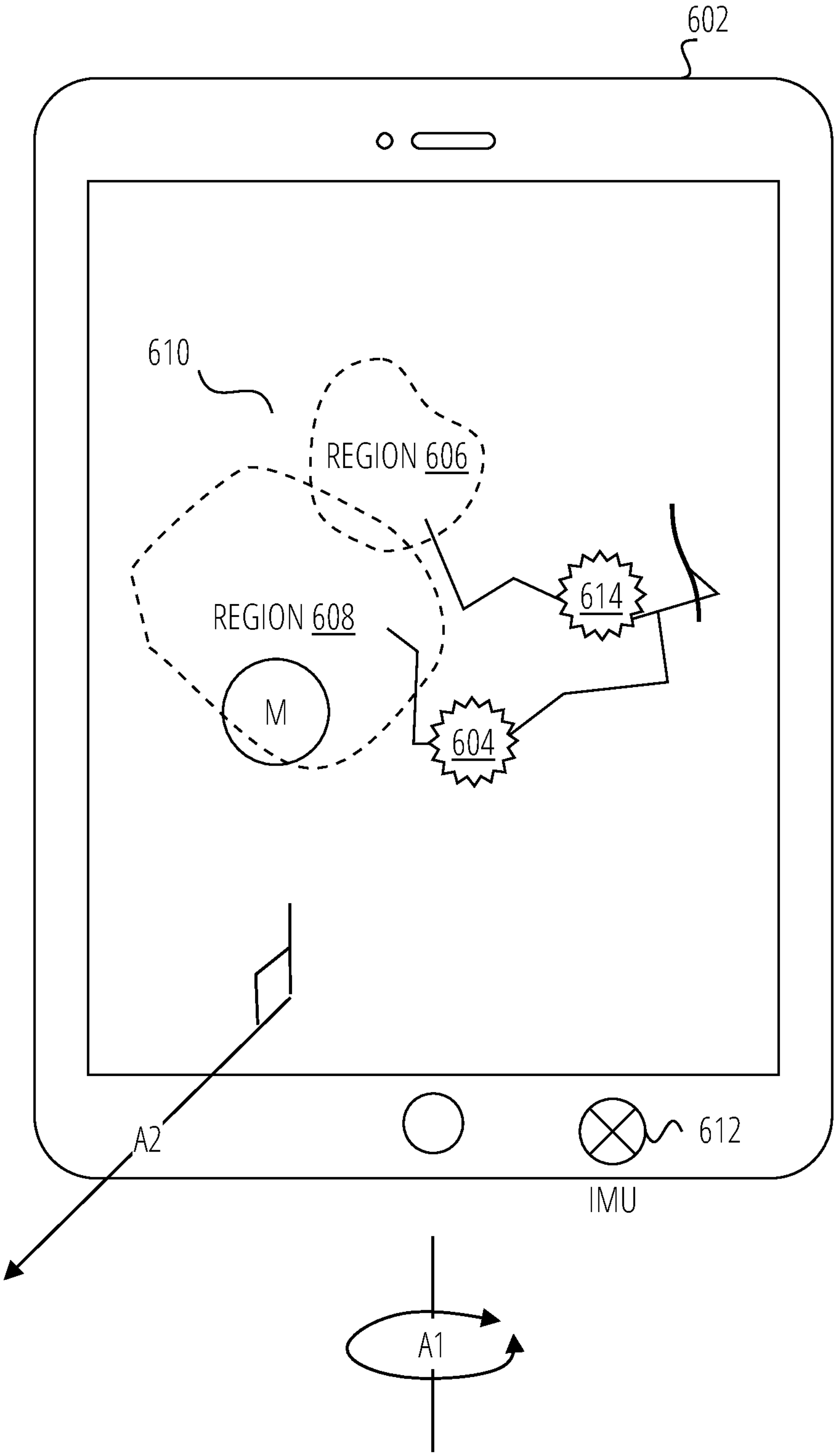
FIG. 6 illustrates an aspect of the subject matter, in accordance with one embodiment.

FIG. 6 shows an example of a device 602 for selecting and displaying a three-dimensional model of a patient, in accordance with some embodiments. Working in 3D models is prone to human error. For example, to navigate a three-dimensional model of human anatomy 610, a user may manually 'pinch', or 'drag' portions of the screen to cause a change in angle, zoom level, or viewing position of the model. Other controls such as buttons may be provided through a user interface to help a user change an orientation of the model or reduce occlusion of a desired object by other structures.

Device 602 may include processing logic that performs the methods and processes described in other sections. Device 602 may provide access to medical images of a patient that are acquired before the procedure (e.g., based on a CT scan and segmentation), and display a three-dimensional model 610 of a patient. Such imagery may improve intraoperative decision-making, such as where to optimally place surgical clips for performing a surgical operation. Digital Imaging and Communications in Medicine (DICOM) describes a standard defining how medical images and their metadata are stored and exchanged. In some instances, the three-dimensional model may be a DICOM image.

Available systems for viewing medical images intraoperatively typically rely on mouse input or touch screen interactions. In the case of mouse input, surgeons need to put on extra gloves to reduce the risk of contamination. The same applies to touch screens as the surface might become dirty and thus obstruct the view. Furthermore, displaying medical images that often show complex 3D structures on 2D screens may lead to a loss of information. Conveying all this information to the user may, in some instances, be best performed using a 3D monitor.

In some examples, the device 602 may adjust a view of the three-dimensional model 610 to show the region (e.g., region 608 or region 606) in front of other structures in the three-dimensional model, based on a tracked position of the display. The device may track its position in physical space based on sensors such as inertial measurement unit (IMU) 612. IMU 612 may include a sensor such as an accelerometer, a gyroscope, or other sensor or combination thereof, that measures and reports a force, angular rate, or orientation of the device 602. A user may interact with the three-dimensional model based on IMU measurements.

In some embodiments, the three-dimensional model 610 is displayed from the perspective of a virtual camera. A user can change the position (e.g., angle or location) of the virtual camera based on moving the device 602. For example, the user may change the rotation, inclination, or position of the tablet as they hold it in their hands. The device may change the pose of the virtual camera in response to the IMU measurement. The device may map or translate the rotation, inclination, or position from the IMU to a virtual position of the virtual camera.

Unlike touch screen gestures that users need to know about from previous experience or instructions, the user's manipulation of the device provides continuous feedback to the user which makes control of the three-dimensional image more intuitive. In some examples, by rotating the device 602, the rendering of the three-dimensional model 610 (e.g., reconstructed data or segmentations) may also be rotated. The amount the device rotates the model 610 may be in proportion to, or in relation to, the amount the user rotates the device. For example, the user may rotate the device according to an axis A1, which may rotate the three-dimensional model 610. The device may increase the rotation of the model 610 as an angle of the device increases. The rotation may cause the virtual camera position to rotate around regions 608 and 606, such that the desired view is shown to the user. If the user wishes to put region 608 at the forefront, the user may rotate or angle the device 602 until virtual camera is positioned so that the region 608 is centered or not occluded, or both. Similarly, if the user wishes to see a clearer angle of region 606, the user may rotate or angle the device 602 until the virtual camera is positioned to show region 606 at the center or un-occluded, or both.

In some examples, when changing the inclination in one axis, the virtual camera rotates around the same axis in the other direction as the tablet device does. In some examples, the virtual camera rotates around the center of all visible objects. Movement of the virtual objects may "follow" movement of the tablet device in the sense that the virtual camera does not move if the tablet device stays in one pose. A virtual object may be a segmented portion of the three-dimensional image. In some examples, the device may compute the orientation of the centroid of the structure with respect to the origin (display). This ensures that the structure is maintained as centered in the view and that the structure is not occluded and is at maximum visibility considering the dimensionality loss from 3D to 2D. For example, region 608 may have a centroid (a center point) with respect to the origin of the display. Similarly, region 606 may have a centroid with respect to the origin of the display. The tablet may be inclined or rotated so that the virtual camera rotates around the centroid of an object in focus.

In some examples, bringing the virtual camera closer or farther away to the displayed objects ("zoom") can be achieved by moving the tablet device along an axis (e.g., A2) which may be perpendicular to the screen surface of device 602. For translating the focal point of the virtual camera ("pan"), users can move the tablet device in the plane defined by the screen surface. A calibration step may be performed before beginning to interact with the system. During calibration, a user may hold the tablet device in a "neutral" pose of their choosing that they like as a starting pose. A user may press a hardware or on-screen button, and the pose is being saved by the system.

In some examples, the device 602 may adjust a view of the three-dimensional model 610 to show the region in front of other structures in the three-dimensional model, based on a selection of the region. For example, the user may select region 606 through a touch screen interface on the device. In response, the device may move its virtual camera position so that region 606 is not occluded, or so that region 606 is centered, or both. Similarly, the user may select a clip position such as 604 or 614 and the device will adjust the virtual camera position to show the clip position centered or not occluded or both. This position change may be performed without additional user input such as 'pinching' or 'dragging' of the display to manually move the virtual camera. By automatically orienting the 3D model based on the target structure being selected, the interactions described may reduce human error of poor rotation and viewing angle of the model.

Another aspect of the disclosure here is a method, performed by a processing device, comprising: obtaining a three-dimensional model of a patient including one or more blood vessels and a mass that is marked for removal; selecting a first position of a first surgical clip from a plurality of potential positions associated with the one or more blood vessels, based on which of the plurality of potential positions is associated with restricting blood flow to a region with a highest amount of the mass with respect to an amount of healthy tissue; in response to an amount of the mass that is included in a cumulative region of selected surgical clips not satisfying a threshold, selecting a second position of a second surgical clip from remaining ones of the plurality of potential positions, based on which of the remaining ones has the highest amount of the mass with respect to an amount of healthy tissue; and presenting, to a display, the three-dimensional model of the patient including the first position and the second position. The method may further comprise determining the region of the three-dimensional model where blood flow is determined to be restricted from for each of the plurality of potential positions associated with the one or more blood vessels, and sorting the plurality of positions based on the amount of the mass with respect to the amount of healthy tissue associated with each of the plurality of positions, wherein an order of the sorting of the plurality of positions is used to select the first position and the second position. In one example, selecting the first position of the first surgical clip and selecting the second position of the second surgical clip are performed in response to one or more criteria not being exceeded. This selection of the first position of the first surgical clip, or of the second position of the second surgical clip, or of one or more additional surgical clips may be repeated until the amount of the mass that is included in the cumulative region of selected surgical clips satisfies the threshold without exceeding one or more criteria.

Yet another aspect of the disclosure here is a system comprising: a display, and a processor, configured to: obtain a three-dimensional model of a patient including one or more blood vessels and a mass that is marked for removal; determine a position of each of one or more surgical clips within the three-dimensional model, wherein blood flow is restricted from a region of the three-dimensional model based on the one or more blood vessels of the three-dimensional model and the position of each of the one or more surgical clips; and present, to the display, the three-dimensional model of the patient including a visual indication of the region and the mass. In one example, determining the position of each of the one or more surgical clips includes automatically selecting a first position that is associated with a highest ratio of a volume of the mass that is included in the region relative to a volume of healthy tissue that is included in the region. In still another example, determining the position of each of the one or more surgical clips includes automatically selecting a next position that is associated with a next highest ratio of the volume of the mass that is included in the region relative to the volume of healthy tissue that is included in the region, and repeating the selecting based on the next highest ratio, without exceeding one or more criteria. The one or more criteria may include a maximum number of allowed surgical clips, or a maximum volume of healthy tissue that is allowed in the region. In another example, determining the position of each of the one or more surgical clips includes selecting the position of each of the one or more surgical clips until a minimum portion of the mass is included in the region. In yet another example, determining the position of each of the one or more surgical clips includes selecting the position of each of the one or more surgical clips to not encroach on a minimum distance between the mass and the position of each of the one or more surgical clips. In one instance, obtaining the three-dimensional model of the patient includes obtaining one or more computerized tomography (CT) scans of the patient, performing segmentation on the one or more CT scans to define structures in the three-dimensional model including the mass that is marked for removal and the one or more blood vessels of the patient. The system may also be configured to adjust a view of the three-dimensional model to show the region in front of other structures in the three-dimensional model, based on a selection of the region, or based on a tracked position of the display.

Some portions of the preceding detailed descriptions have been presented in terms of algorithms and symbolic representations of operations on data bits within a computer memory. These algorithmic descriptions and representations are the ways used by those skilled in the data processing arts to convey the substance of their work most effectively to others skilled in the art. An algorithm is here, and, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the disclosure also relate to an apparatus for performing the operations herein. Such a computer program is stored in a non-transitory computer readable medium. A machine-readable medium includes any mechanism for storing information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices).

The processes or methods depicted in the preceding figures may be performed by processing logic that comprises hardware (e.g., circuitry, dedicated logic, etc.), software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Embodiments of the present disclosure are not described with reference to any programming language. It will be appreciated that a variety of programming languages may be used to implement the teachings of embodiments of the disclosure as described herein.

In the foregoing specification, embodiments of the disclosure have been described with reference to specific exemplary embodiments thereof. It will be evident that various modifications may be made thereto without departing from the broader spirit and scope of the disclosure as set forth in the following claims. The specification and drawings are, accordingly, to be regarded in an illustrative sense rather than a restrictive sense. The foregoing description, for purposes of explanation, used specific nomenclature to provide a thorough understanding of the invention. However, it will be apparent to one skilled in the art that specific details are not required to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described to best explain the principles of the invention and its practical applications, and they thereby enable others skilled in the art to best utilize the invention and various embodiments with various modifications as are suited to the particular use contemplated. It is intended that the following claims and their equivalents define the scope of the invention.

What is claimed is:

1. A method, performed by a processing device, comprising:

constructing a three-dimensional (3D) anatomy model including one or more blood vessels associated with a marked mass for removal;

selecting a first position for a first surgical clip to be applied to the one or more blood vessels;

using the 3D anatomy model and the first position to determine a first region of the 3D anatomy model that includes the marked mass and surrounding healthy tissue occluded by the first surgical clip;

determining a volume of the marked mass that is within the first region;

determining, without user interference, whether the volume of the marked mass is less than a threshold volume of mass;

responsive to determining that the volume of the marked mass is less than the threshold volume of mass, selecting a second position for a second surgical clip to be applied and using the 3D anatomy model, the first position, and the second position to determine a cumulative region that comprises the first region and a second region of the 3D anatomy model occluded by the first surgical clip and the second surgical clip, respectively; and displaying the 3D anatomy model including the first position for the first surgical clip and the second position for the second surgical clip.

2. The method of claim 1, further comprising displaying a visual indication of the cumulative region and the marked mass.

3. The method of claim 1, wherein an order of selecting the first position and selecting the second position is based on the volume of the marked mass relative to a volume of the surrounding healthy tissue that is associated with each of the first position and the second position, respectively.

4. The method of claim 1, further comprising, responsive to the volume of the marked mass satisfying the threshold volume of mass, not selecting the second position of the second surgical clip or any additional positions for any additional surgical clips.

5. The method of claim 1, wherein the marked mass is a first portion of a total marked mass, and the volume is a first volume of the first portion, wherein the second region includes a second portion of the total marked mass, wherein the method further comprises;

determining a second volume of the second portion within the second region; and selecting an additional position for an additional surgical clip in response to a total volume of the marked mass that includes at least the first volume and the second volume included in the cumulative region of selected surgical clips not satisfying the threshold volume of mass and in response to one or more criteria not being satisfied.

6. The method of claim 5, wherein the one or more criteria include a maximum number of allowed surgical clips.

7. The method of claim 5, wherein the one or more criteria include a maximum volume of healthy tissue that is allowed in the cumulative region.

8. The method of claim 1, wherein the threshold volume of mass is obtained from a configurable setting.

9. The method of claim 1, wherein selecting the first position and the second position includes enforcing a minimum distance between the marked mass and the first surgical clip, and between the marked mass and the second surgical clip.

10. The method of claim 1, wherein constructing the 3D anatomy model includes obtaining one or more scans of a patient anatomy, performing segmentation on the one or more scans to define structures of the patient anatomy including the marked mass and the one or more blood vessels.

11. The method of claim 1, wherein displaying the 3D anatomy model includes adjusting a view of the 3D anatomy model to show the first region in front of other structures in the 3D anatomy model, based on a selection of the first region.

12. The method of claim 1, wherein displaying the 3D anatomy model includes presenting the 3D anatomy model on a portable device and adjusting a view of the 3D anatomy model to show the first region or the second region in front of other structures in the 3D anatomy model, based on a tracked position of the portable device.

13. A system comprising:

a display, and a processor, configured to:

obtain a three-dimensional (3D) model of a patient including one or more blood vessels and a mass that is marked for removal;

determine a first position of a first surgical clip to be applied to a first blood vessel;

use the 3D model and the first position to determine a first region of the 3D model that includes the mass and surrounding healthy tissue occluded by the first surgical clip;

determine a volume of the mass that is within the first region;

determine, without user interference, whether the volume of the mass is less than a threshold volume of mass;

responsive to determining that the volume of the mass is less than the threshold volume of mass, determine a second position of a second surgical clip to be applied to a second blood vessel and use the 3D model, the first position, and the second position to determine a second region of the 3D model occluded by both surgical clips; and present, to the display, the 3D model of the patient including a visual indication of the second region and the mass.

14. The system of claim 13, wherein the display and the processor are integral to a tablet computer.

15. The system of claim 13, wherein the processor is configured to determine the first position or the second position by obtaining user input indicating the first position or the second position on a portion of the first blood vessel or a portion of the second blood vessel, respectively.

16. The system of claim 13, wherein the processor is further configured to display a first volume of the second region that is associated with the mass that is marked for removal and a second volume of the second region that is associated with healthy tissue.

17. The system of claim 13, wherein the processor is configured to determine the first position and the second position by automatically selecting the first position and the second position such that the second region comprises a highest ratio of volume of the mass relative to volume of healthy tissue that is included in the second region.

18. A system comprising:

a display, and a processor, configured to:

obtain a three-dimensional (3D) model of a patient including one or more blood vessels and a mass that is marked for removal;

determine, without user interference, a position of each of one or more surgical clips within the 3D model among a plurality of potential surgical clip positions associated with the one or more blood vessels, to 1) increase a volume of the mass that is included in a region of the 3D model and 2) reduce a volume of healthy tissue that is in the region, wherein blood flow is restricted from the region based on the one or more blood vessels of the 3D model and the position of each of the one or more surgical clips; and present, to the display, the 3D model of the patient including a visual indication of the region and the mass.

19. The system of claim 18, wherein the plurality of potential surgical clip positions are a part of a predefined surgical clip list of potential surgical clip positions, wherein the processor is configured to determine the position of each of the one or more surgical clips by iteratively selecting surgical clips from the predefined surgical clip list until the volume of the mass exceeds a mass volume threshold or the volume of the healthy tissue exceeds a healthy tissue threshold.

20. The system of claim 19, wherein the predefined surgical clip list is sorted in a descending order from a most amount of mass included in the region, a lowest amount of healthy tissue included in the region, or a ratio of a combination thereof, wherein the surgical clips are iteratively selected from the predefined surgical clip list in the descending order.

* * * * *